(12) United States Patent
Fukumoto et al.

(10) Patent No.: US 9,642,938 B2
(45) Date of Patent: May 9, 2017

(54) MEDICAL COMPOSITION AND MEDICAL KIT

(75) Inventors: Shinya Fukumoto, Osaka (JP); Hidenori Koyama, Izumi (JP); Yoshiki Nishizawa, Osaka (JP); Tsutomu Furuzono, Sennan-gun (JP); Masahiro Okada, Kobe (JP)

(73) Assignees: OSAKA CITY UNIVERSITY, Osaka (JP); JAPAN HEALTH SCIENCES FOUNDATION, Tokyo (JP)

( * ) Notice: Subject to any disclaimer, the term of this patent is extended or adjusted under 35 U.S.C. 154(b) by 0 days.

(21) Appl. No.: 13/000,838

(22) PCT Filed: Jun. 26, 2009

(86) PCT No.: PCT/JP2009/061726
§ 371 (c)(1),
(2), (4) Date: Dec. 22, 2010

(87) PCT Pub. No.: WO2009/157543
PCT Pub. Date: Dec. 30, 2009

(65) Prior Publication Data
US 2011/0104292 A1    May 5, 2011

(30) Foreign Application Priority Data
Jun. 27, 2008  (JP) ................. 2008-169433

(51) Int. Cl.
| | |
|---|---|
| A61K 9/16 | (2006.01) |
| A61K 31/74 | (2006.01) |
| A01N 63/00 | (2006.01) |
| A61L 27/38 | (2006.01) |
| A61L 27/32 | (2006.01) |
| A61L 27/54 | (2006.01) |
| A61L 27/56 | (2006.01) |
| A61L 27/58 | (2006.01) |

(52) U.S. Cl.
CPC ........... *A61L 27/3804* (2013.01); *A61L 27/32* (2013.01); *A61L 27/54* (2013.01); *A61L 27/56* (2013.01); *A61L 27/58* (2013.01); *A61K 9/16* (2013.01); *A61K 31/74* (2013.01); *A61L 2300/414* (2013.01); *A61L 2300/426* (2013.01)

(58) Field of Classification Search
CPC ........... A61K 9/16; A61K 31/74; A61L 27/32; A61L 27/3804; A61L 27/56; A61L 27/58; A61L 2300/414; A61L 2300/426
USPC .................... 424/78.08, 93.1, 490
See application file for complete search history.

(56) References Cited

U.S. PATENT DOCUMENTS

| | | | |
|---|---|---|---|
| 6,344,209 B1 | 2/2002 | Saito et al. | |
| 7,473,731 B2 | 1/2009 | Furuzono et al. | |
| 2003/0162287 A1 | 8/2003 | Yamamoto et al. | |
| 2003/0171287 A1 | 9/2003 | Morishita et al. | |
| 2004/0228848 A1* | 11/2004 | Har-Noy | |
| 2005/0119732 A1 | 6/2005 | Furuzono et al. | |
| 2006/0104942 A1* | 5/2006 | Fukuda et al. | |
| 2007/0141111 A1* | 6/2007 | Suokas et al. | |
| 2007/0202594 A1 | 8/2007 | Yamamoto et al. | |
| 2007/0259181 A1* | 11/2007 | Furuzono et al. | |
| 2008/0065046 A1* | 3/2008 | Sabbah et al. | |
| 2009/0291087 A1* | 11/2009 | Scott et al. | |
| 2010/0143311 A1* | 6/2010 | Mizukami et al. | |
| 2010/0240735 A1 | 9/2010 | Morishita et al. | |
| 2013/0085108 A1 | 4/2013 | Cho et al. | |
| 2013/0156787 A1 | 6/2013 | Lee et al. | |

FOREIGN PATENT DOCUMENTS

| | | |
|---|---|---|
| JP | 05-17111 | 1/1993 |
| JP | 2000-005298 | 1/2000 |
| JP | 2002-137910 | 5/2002 |
| JP | 2004-167202 | 6/2004 |
| JP | 2004-210848 | 7/2004 |
| JP | 2005-052224 | 3/2005 |
| JP | 2005-279138 | 10/2005 |
| JP | 2006-006125 | 1/2006 |
| JP | 2006-130007 | 5/2006 |
| JP | 2008-126005 | 6/2008 |
| KR | 10-0798566 | 1/2008 |
| KR | 10-1234807 | 2/2013 |
| KR | 10-1297037 | 8/2013 |
| WO | 03/088925 | 10/2003 |
| WO | 2004/075939 | 9/2004 |

OTHER PUBLICATIONS

Rizzi et al., 2001, Journal of Biomedical Materials and research, vol. 55, p. 475-486.*
Marra et al., 1999, J Biomed Mater res, vol. 47, p. 324-335.*
Zhao et al., 2006, Biomaterials, vol. 27, p. 1859-1867.*
Wei et al., 2004, Biomaterials, vol. 25, p. 4749-4757.*
Sato et al., 2003, Developmental Biology, vol. 260, p. 404-413.*
Abeyta et al., 2004, Human Molecular Genetics, vol. 13, No. 6, p. 601-608.*
Kolf et al., 2007, Arthritis Research & Therapy, vol. 9, p. 204, 10 pages.*
Alenzi et al., 2011, African Journal of Biotechnology, vol. 10(86), pp. 19929-19940.*
Choong et al., 2006, Tissue Engineering, vol. 12, No. 9, p. 2521-2531.*
Tamai et al., 1999, Journal of Colloid and Interface Science, vol. 212, p. 585-588.*

(Continued)

*Primary Examiner* — Shin Lin Chen
(74) *Attorney, Agent, or Firm* — Nixon & Vanderhye PC

(57) ABSTRACT

In order to provide (i) a medical composition that has a strong angiogenic effect, has low invasiveness to a body of a patient, and is easy to administer to a living subject and (ii) a medical kit using a medical composition, the medical composition includes: a carrier in a particle form, the carrier having (a) a support made from a bioabsorbable polymer and (b) a surface layer made from hydroxyapatite and provided on the support; and cells provided on a surface of the carrier.

8 Claims, 9 Drawing Sheets

(56) References Cited

OTHER PUBLICATIONS

Figure 1:
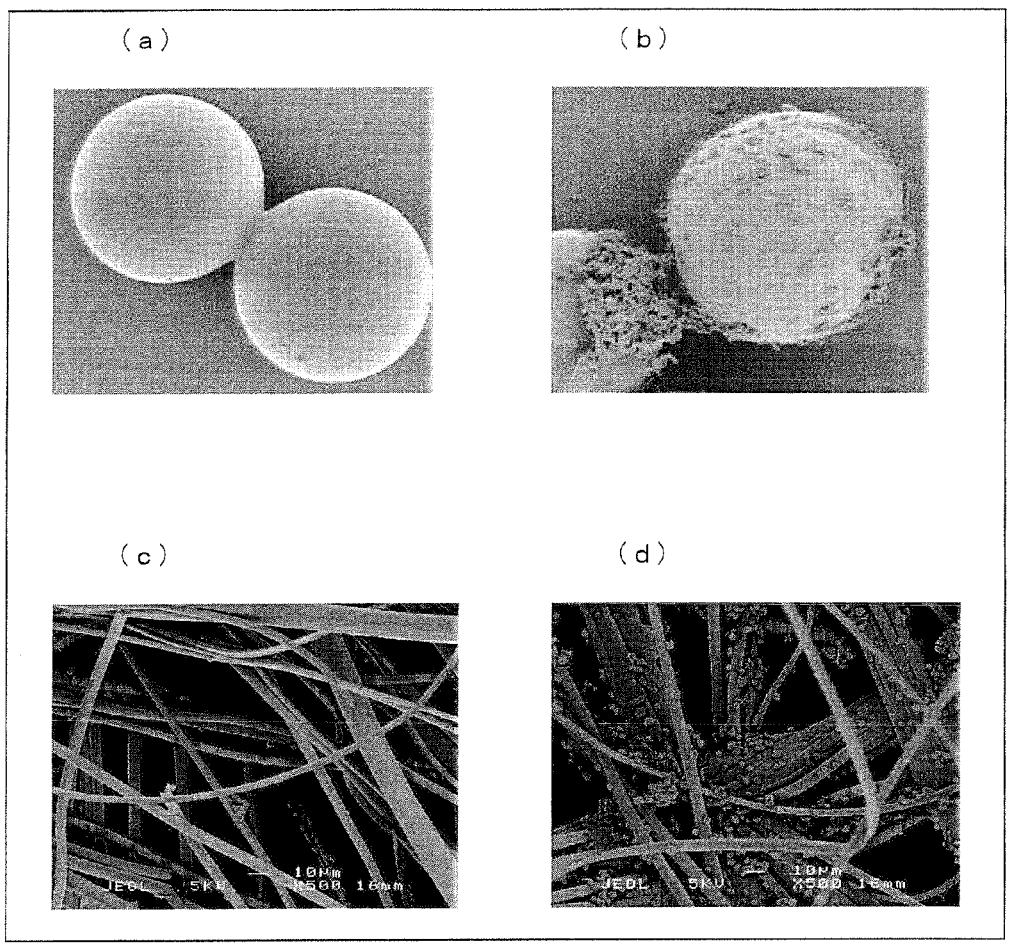

T. Asahara et al., "Isolation of Putative Progenitor Endothelial Cells for Angiogenesis" Science, 275: pp. 964-967, 1997.

T. Murayama et al. "Bone marrow-derived endothelial progenitor cells for vascular regeneration" Curr. Opin. Mol. Ther., 4: pp. 395-402, 2002.

E. Tateishi-Yuyama et al. "Therapeutic angiogenesis for patients with limb ischaemia by autologous transplantation of bone-marrow cells: a pilot study and a randomised controlled trial" Lancet, 360: pp. 427-435, 2002.

S. Fukumoto et al. Effectiveness of Autologous Implantation of Bone Marrow-Mononuclear Cells for Severe Limb Ischemia-Study Involving Hemodialysis Patients—Toseki Kaishi, 37; pp. 1493-1501, 2004.

V.J. Dzau et al. "Therapeutic Potential of Endothelial Progenitor Cells in Cardiovascular Diseases" Hypertension, 46: pp. 7-18, 2005.

H.F. Tse et al. "Therapeutic Angiogenesis with Bone Marrow-Derived Stem Cells" J. Cardiovasc Pharmacol Ther., 12: pp. 89-97, 2007.

M. Miyoshi et al. "Effects of bFGF Incorporated into a gelatin sheet on wound healing" J. Biomater. Sci., Polymer, Edn. 2005, 16, pp. 893-907.

Y. Sakakibara et al. "Prevascularization with gelatin microspheres containing basic fibroblast growth factor enhances the benefits of cardiomyocyte transplantation" J. Thorac. Cardiovasc. Surg. 2002, 124: pp. 50-56.

T. Kinnaird et al. "Local Delivery of Marrow-Derived Stromal Cells Augments Collateral Perfusion Through Paracrine Mechanisms" Circulation, 109: pp. 1543-1549, 2004.

H. Maeda et al. "Fabrication of apatite nanocrystal /poly(L-lactic acid) nanocomposites" The Adhesion Society of Japan. 46th Annual Conference Presentation Summaries (Jun. 2008), pp. 25-26.

H. Maeda et al. "Development of poly(L-lactic acid) composite particles via multiple emulsion stabilized by apatite nanocrystal" Polymer Preprints, Japan vol. 57, No. 1 57th SPSJ Annual Meeting May 28-30, 2008, pp. 1813.

S. Fujii et al. "Preparation of Pickering-type Emulsions Stabilized by Bioceramics/Polyester Interaction at Oil/Water Interface" Abstracts Eighth International Symposium on Biomimetic Materials Processing. 2008, pp. 82.

Office Action from the Japanese Patent Office and its English translation for related application JP 2008-169433, mailed Mar. 5, 2013.

Nakamura et al. "Tissue-hydroxyapatite composites, and production thereof" Chemical Abstract Database accession No. 2008-665944, abstract for JP 2008-126005, two pages (Jun. 2008).

Notice of Reasons for Rejection and its English translation for Application No. JP 2008-169433, five pages, dated Nov. 27, 2012.

Extended Search Report for Application No. EP 09770253.4, six pages, dated Dec. 21, 2012.

Hao et al. "Repairing articular cartilage full-thickness defects with homograft of mesenchymal stem cells seeded onto novel scaffold composites hydroxyapatite/calcium polyphosphate/poly-L-lactide" *Chinese Journal of Clinical Rehabilitation* 10:1-13 (Oct. 2006).

Office Action from the Chinese Patent Office and its English translation for related application CN 200980123603.8, mailed Oct. 15, 2013.

Zhang et al. In *Clinical Vascular Surgery* (Science Press, Beijing CN) p. 241 and partial English translation (Jan. 2007).

Takeda et al. "Injectable cell scaffold restores impaired cell-based therapeutic angiogenesis in diabetic mice with hindlimb ischemia" *Biochemical and Biophysical Research Communications* 454:119-124 (Nov. 2014).

\* cited by examiner

FIG. 3
(a)
Incision Transplantation
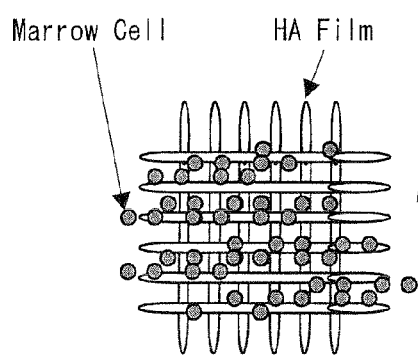
Marrow Cell    HA Film
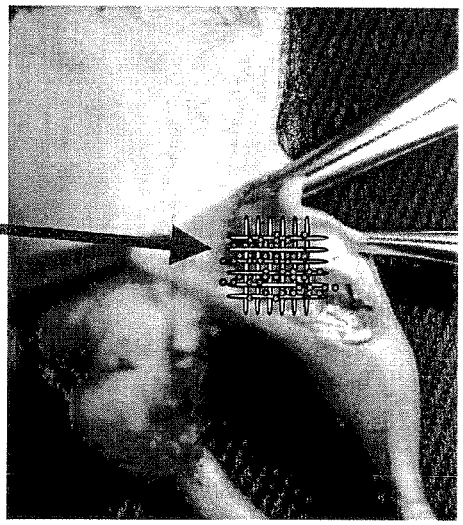
(b)
Intramuscular Administration
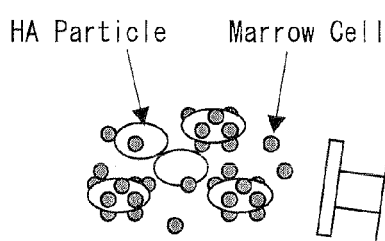
HA Particle    Marrow Cell
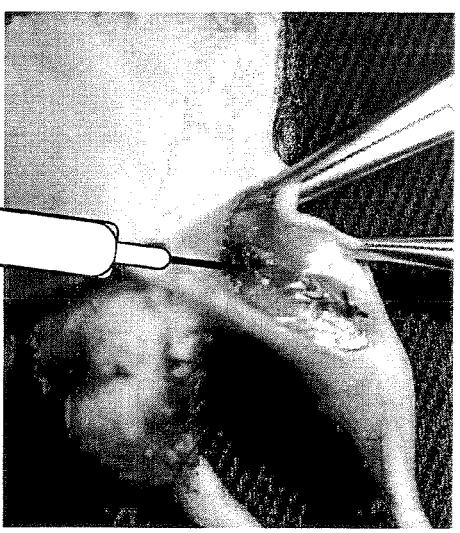

FIG. 4
(a)
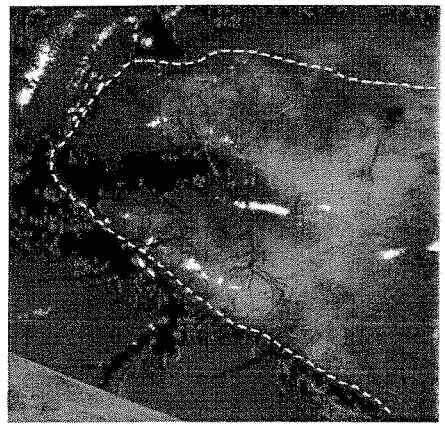
(b)
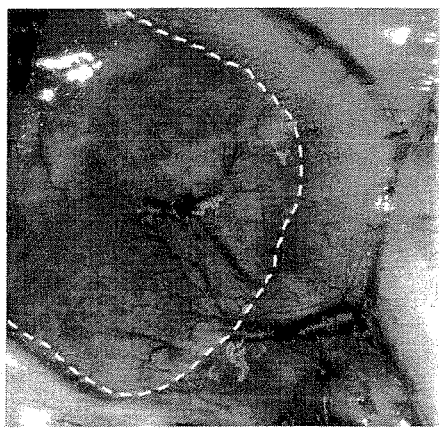
(c)

FIG. 8
(a)
Marrow Cells Only
Day8
Marrow Cells + HAp Particles
Day8
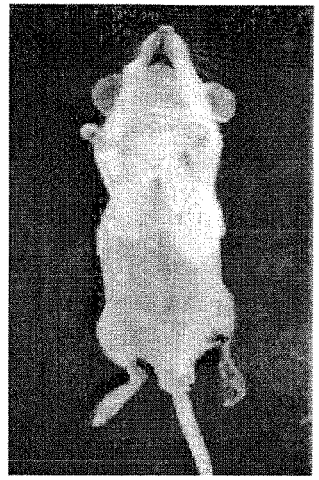
(b)
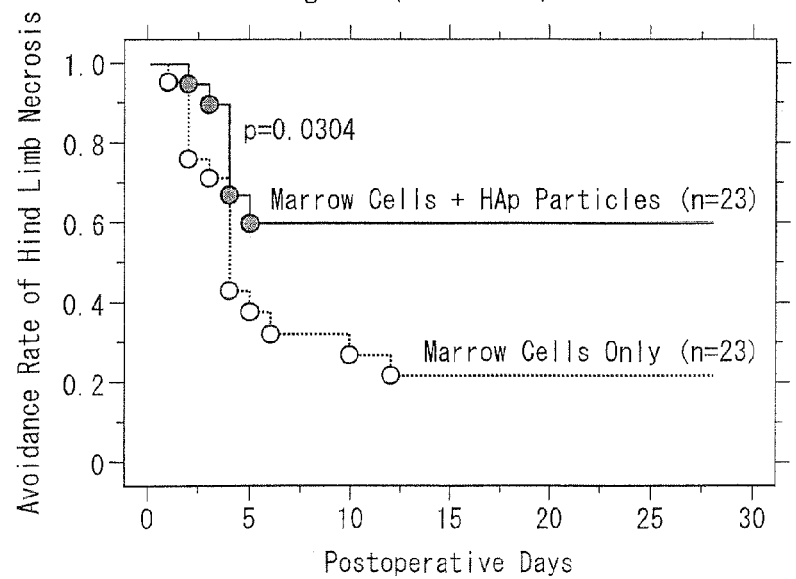

MEDICAL COMPOSITION AND MEDICAL KIT

This application is the U.S. national phase of International Application No. PCT/JP2009/061726, filed 26 Jun. 2009, which designated the U.S. and claims priority to Japanese Patent Application No. 2008-169433, filed 27 Jun. 2008, the entire contents of each of which are hereby incorporated by reference.

TECHNICAL FIELD

The present invention relates to a medical composition and a medical kit, each of which can induce angiogenesis.

BACKGROUND ART

As the numbers of diabetic patients and patients with chronic renal failure have increased in recent years, an increased number of such patients develop a peripheral arterial disease (e.g., arteriosclerosis obliterans or the like) as a complication of the diabetes or of the chronic renal failure. The peripheral arterial disease is such that, for example, a limb peripheral artery is narrowed and/or obstructed, thereby causing an intractable ulcer and/or gangrene. As the intractable ulcer and/or gangrene progresses, amputation of the affected limb may be necessary. In recent years, the number of patients with such severe conditions has also been increased.

In 1997, Asahara et al. isolated and identified vascular endothelium precursor cells from adult human peripheral blood (for example, refer to Non Patent Literature 1). After that, it was found that multipotent stem cells or vascular endothelium precursor cells, which are present in marrow, participated in normal angiogenesis and abnormal angiogenesis (i.e., participated in vascular development) in various tissues (for example, refer to Non Patent Literature 2).

On the basis of these findings, the following attempt has been carried out. That is, multipotent stem cells etc., which are isolated from marrow or from peripheral blood, are directly implanted into an ischemic lower limb or into ischemic myocardium so as to induce angiogenesis, thereby restoring normal blood flow (angiogenesis therapy by cell transplantation).

For example, myelomonocytic cell autotransplantation for ischemia of a human lower limb started in the end of 2000 in Japan ahead of any other countries in the world. Today, the myelomonocytic cell autotransplantation is being carried out in more than a dozen facilities all over Japan (for example, refer to Non Patent Literature 3). Specifically, at Osaka City University, (i) 11 cases of the myelomonocytic cell autotransplantation has been performed for chronic severe ischemia (including 3 cases of dialysis patients) and (ii) 11 cases of transplantation of peripheral-blood mononuclear cells has been performed for chronic severe ischemia (including 2 cases of dialysis patients), from 2002 to date. Note here that, an efficacy rate of the myelomonocytic cell autotransplantation in total was 62.5%, and an efficacy rate of the myelomonocytic cell autotransplantation for dialysis patients was 33.3% (for example, refer to Non Patent Literature 4).

Recently, the following methods have also been attempted. That is, for example, (i) a method of implanting concentrated CD34 positive cells, which are immature marrow cells (for example, refer to Non Patent Literature 5) and (ii) a method of using, during the transplantation of peripheral-blood mononuclear cells, a granulocyte proliferation factor (G-CSF) together with the peripheral-blood mononuclear cells (for example, refer to Non Patent Literature 6). However, these methods have not given results that are more excellent in efficacy rate than those obtained by the original method.

Further, an attempt has been carried out to use vascular growth cytokine (such as bFGF) in ulcer treatment or in angiogenesis therapy. Specifically, vascular growth cytokine is supported by a carrier such as gelatin hydrogel (for example, refer to Non Patent Literature 7) or by gelatin microsphere (for example, refer to Non Patent Literature 8), and then the carrier is administered into a living subject.

Furthermore, recently, it has been proposed to induce angiogenesis by immobilizing cells to an artificial carrier and then insert the artificial carrier into a living subject (for example, refer to Patent Literature 1).

CITATION LIST

Patent Literature

Patent Literature 1
Japanese Patent Application Publication, *Tokukai*, No. 2004-51952 A (Publication Date: Feb. 19, 2004)

Non Patent Literatures

Non Patent Literature 1
Science, 275:964-967, 1997
Non Patent Literature 2
Curr. Opin. Mol. Ther., 4:395-402, 2002
Non Patent Literature 3
Lancet, 360:427-435, 2002
Non Patent Literature 4
Journal of Japanese Society for Dialysis Therapy, 37:1493-1501, 2004
Non Patent Literature 5
Hypertension, 46:7-18, 2005
Non Patent Literature 6
J. Cardiovasc Pharmacol Ther., 12:89-97, 2007
Non Patent Literature 7
J. Biomater. Sci., Polym. Eds., 2005, 16, 893-902
Non Patent Literature 8
J. Thorac. Cardiovasc. Surg. 2002, 124:50-56
Non Patent Literature 9
Circulation, 109:1543-1549, 2004

SUMMARY OF INVENTION

Technical Problem

Note, however, that the conventional angiogenesis therapy has involved a problem in which (i) new blood vessels cannot be sufficiently generated and also (ii) the conventional angiogenesis therapy is highly invasive to the body of a patient.

It has been recently found that, according to the angiogenesis therapy by cell transplantation, only less than 10% of transplanted cells are incorporated in structures of newly-generated blood vessels. Further, it has been believed that an important factor for angiogenesis is the other major part of the transplanted cells locally secrete several kinds of cytokine (for example, refer to Non Patent Literature 9).

However, it is known that, according to the conventional angiogenesis therapy by cell transplantation, 70% to 80% of the transplanted cells begin circulating in the body within 48 hours from the transplantation. Therefore, only a small number of the transplanted cells remain in a local site. That is, according to the angiogenesis therapy by cell transplantation, it is not possible to effectively keep the transplanted cells in the local site. As a result, it is not possible to generate new blood vessels sufficiently.

Further, it is known that, according to the conventional angiogenesis therapy by cell transplantation, a curative effect can be enhanced to a certain degree by increasing the number of cells to be transplanted (for example, refer to Non Patent Literature 4). Note here that the cells to be transplanted need to be derived from the body of the patient to be treated. However, in many cases, the entire body of the patient suffering from peripheral arterial disease or the like is in a bad condition. That is, if a large number of cells are obtained from the patient, then a physical burden for the body of the patient will be heavy, i.e., this is highly inventive to the body of the patient.

Further, the conventional angiogenesis therapy using vascular growth cytokine involves the following problems. That is, although a material of biological origin such as gelatin has an excellent bioactivity, such a material involves a lot of problems such as an effect of a chemical cross-linking agent, antigenicity of the material of biological origin, infection of viruses and prion, and the like. That the angiogenesis therapy has a problem in which the carrier is highly invasive to the body of the patient after being implanted into the body of the patient.

Moreover, according to the method disclosed in Patent Literature 1, a carrier inserted in a living subject is not degraded in the living subject. Such a carrier may cause a side effect.

The present invention has been made in view of the problems, and an object of the present invention is to provide (i) a medical composition which (a) has a strong angiogenic effect, (b) has low invasiveness to a body of a patient, and (c) is easy to administer to a living subject, and (ii) a medical kit using a medical composition.

Solution to Problem

The inventors of the present invention have carried out an intensive study in view of the object, and found the following fact. That is, by causing cells to adhere to a carrier coated with hydroxyapatite, it is possible to keep the cells alive in a local site of a patient over a long period of time. This makes it possible to effectively induce angiogenesis even if only a small number of cells are transplanted. In this way, the inventors of the present invention have completed the present invention.

That is, in order to attain the above object, a carrier in a particle form, the carrier having (i) a support made from a bioabsorbable polymer and (ii) a surface layer made from hydroxyapatite and provided on the support; and cells provided on a surface of the carrier.

The medical composition in accordance with the present invention is preferably configured such that the carrier falls within a range of 10 µm to 200 µm in particle diameter.

The medical composition in accordance with the present invention is preferably configured such that the carrier has a porous structure.

The medical composition in accordance with the present invention is preferably configured such that the bioabsorbable polymer is at least one selected from the group consisting of: polylactic acid, polyglycolic acid, polyethylene glycol, propylene glycol, polyhydroxybutylate, polycarbonate, polyamide, cellulose, chitin, chitosan, starch, polyglutamic acid, polydioxanone, cyanoacrylate polymers, polycaprolactone, synthetic polypeptides, hyaluronic acid, polymalic acid, poly butylene succinate, and copolymers of any combination thereof. Alternatively, the bioabsorbable polymer can be synthetic polymer.

The medical composition in accordance with the present invention is preferably configured such that the cells are at least one kind selected from the group consisting of: myelomonocytic cells, peripheral-blood mononuclear cells, multipotent stem cells, hematopoietic stem cells, vascular endothelium precursor cells, iPS cells, ES cells, platelet, and mesenchymal stem cells.

It is preferable that the medical composition in accordance with the present invention further include angiogenesis cytokine provided on the surface of the carrier.

The medical composition in accordance with the present invention is preferably configured such that the angiogenesis cytokine is at least one selected from the group consisting of: aFGF, bFGF, VEGF, HGF, PDGF, PIGF, TNF, EGF, angiopoietin, IL, HAPO, Shh, TGF-β, G-CSF, M-CSF, SCF, EPO, TPO, and Flt.

In order to attain the above object, a medical kit in accordance with the present invention includes: the foregoing medical composition; and an injector for administering the medical composition to a living subject.

In order to attain the above object, a method of producing a medical composition in accordance with the present invention includes: mixing (i) a carrier in a particle form and (ii) cells, the carrier having (a) a support made from a bioabsorbable polymer and (b) a surface layer made from hydroxyapatite and provided on the support.

The method of producing the medical composition in accordance with the present invention is preferably configured such that, in the step of mixing, a number of said cells to be added is less than or equal to $1 \times 10^{10}$ per particle of said carrier.

Advantageous Effects of Invention

As described earlier, a medical composition in accordance with the present invention includes: a carrier in a particle form, the carrier having (i) a support made from a bioabsorbable polymer and (ii) a surface layer made from hydroxyapatite and provided on the support; and cells provided on a surface of the carrier. The medical composition in accordance with the present invention can further include cytokine if needed.

As described earlier, a medical kit in accordance with the present invention includes: the foregoing medical composition; and an injector for administering the medical composition to a living subject.

As described earlier, a method of producing a medical composition in accordance with the present invention includes: mixing (i) a carrier in a particle form and (ii) cells, the carrier having (a) a support made from a bioabsorbable polymer and (b) a surface layer made from hydroxyapatite and provided on the support.

According to the present invention, the medical composition can remain in a local site in a living subject. This makes it possible to effectively generate new blood vessels in a target site.

According to the present invention, the cells are provided on the surface of the carrier. This makes it possible to effectively generate new blood vessels with a small number of cells.

According to the present invention, since the carrier is composed mainly of a bioabsorbable polymer and hydroxyapatite, the medical composition can be degraded and absorbed after inducing angiogenesis. That is, since the medical composition automatically disappears after inducing angiogenesis, it is possible to reduce a burden on a living subject. Further, it is possible to control a degradation speed and absorption speed of the medical composition by changing composition and/or form of the support.

Further, since constituents of the medical composition in accordance with the present invention have a low toxicity to a living subject, it is possible to prevent occurrence of side effects (e.g., inflammation) when the medical composition is administered to the living subject.

Furthermore, since the present invention does not employ animal-derived protein such as collagen or gelatin, it is possible to achieve a high level of biological safety.

Further, since the present invention employs a carrier in a particle form, the carrier can be administered into a living subject with use of an injector. This makes it possible to administer the medical composition by a method with a small burden on a body of a patient, and to easily administer the medical composition to a local site.

Furthermore, according to the present invention, a patient himself can easily administer the medical composition. Accordingly, the present invention makes is possible, even in an aging society, to easily give aid to patients suffering from for example bedsores. As such, it is possible to prevent a reduction in patients' QOL (Quality Of Life) and to reduce medical costs.

BRIEF DESCRIPTION OF DRAWINGS (a) of FIG. 1 is a photomicrograph of marrow cells on polylactic acid particles. (b) of FIG. 1 is a photomicrograph of marrow cells on hydroxyapatite/polylactic acid particles. (c) of FIG. 1 is a photomicrograph of marrow cells on a polylactic acid film. (d) of FIG. 1 is a photomicrograph of marrow cells on a hydroxyapatite/polylactic acid film.

Figure 2:
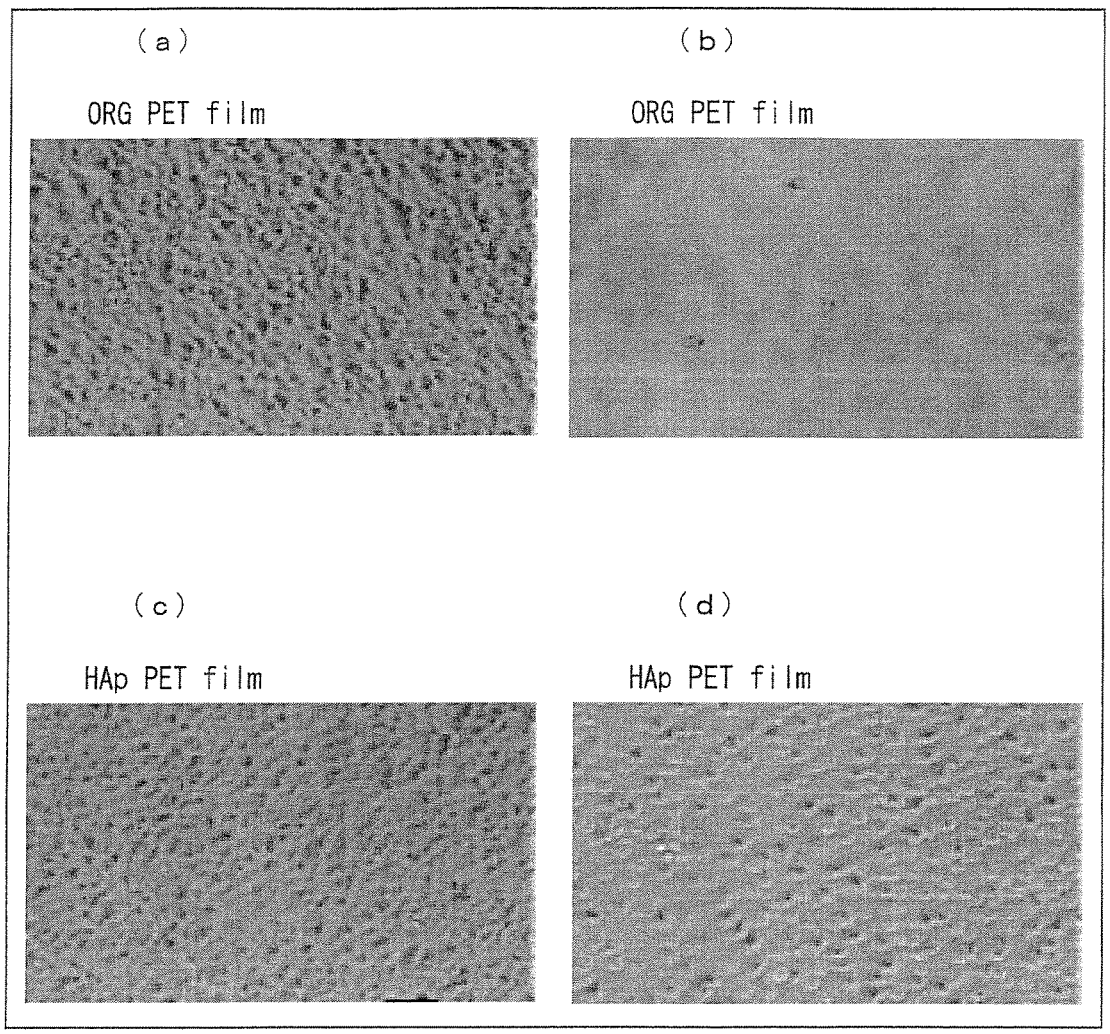

(a) of FIG. 2 is a photomicrograph of a polylactic acid film/L929 cell complex before trypsin treatment. (b) of FIG. 2 is a photomicrograph of the polylactic acid film/L929 cell complex after the trypsin treatment. (c) of FIG. 2 is a photomicrograph of a hydroxyapatite/polylactic acid film/L929 cell complex before trypsin treatment. (d) of FIG. 2 is a photomicrograph of the hydroxyapatite/polylactic acid film/L929 cell complex after the trypsin treatment.

(a) of FIG. 3 is a view schematically illustrating how a hydroxyapatite/polylactic acid film/marrow cell complex in a form of a film is implanted. (b) of FIG. 3 is a view schematically illustrating how hydroxyapatite/polylactic acid particle/marrow cell complexes in a particle form are administered by intramuscular injection.

(a) through (c) of FIG. 4 are photomicrographs each of which shows a site to which a hydroxyapatite/polylactic acid film/marrow cell complex was administered.

Figure 5:
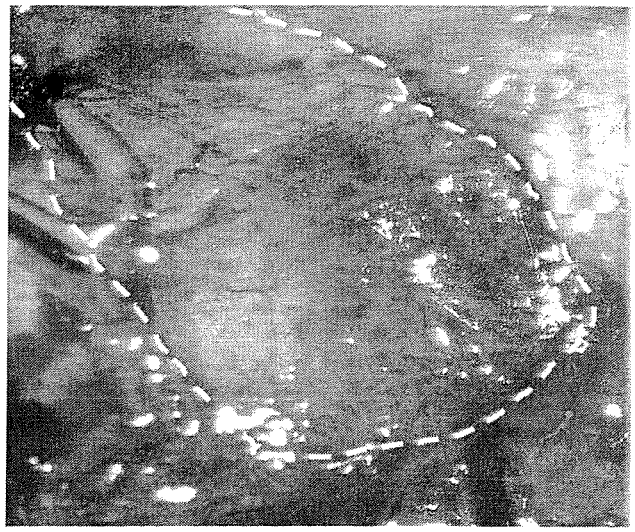

FIG. 5 is a photomicrograph of a site to which a hydroxyapatite/polylactic acid film complex was administered.

Figure 6:
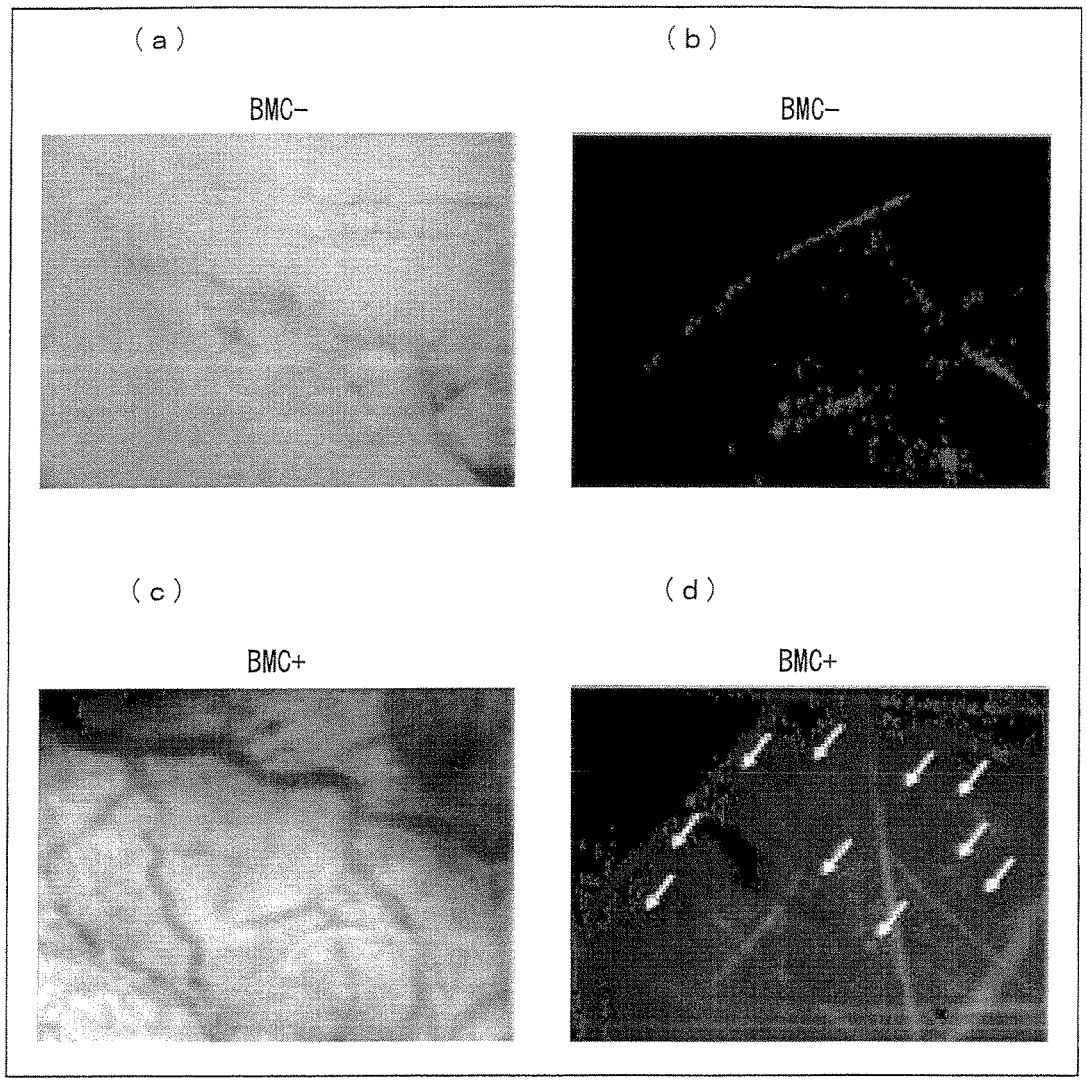

(c) and (d) of FIG. 6 are photomicrographs each of which shows a site to which a hydroxyapatite/polylactic acid film/marrow cell complex was administered. (a) and (b) of FIG. 6 are photomicrographs each of which shows a site to which a hydroxyapatite/polylactic acid film complex was administered.

Figure 7:
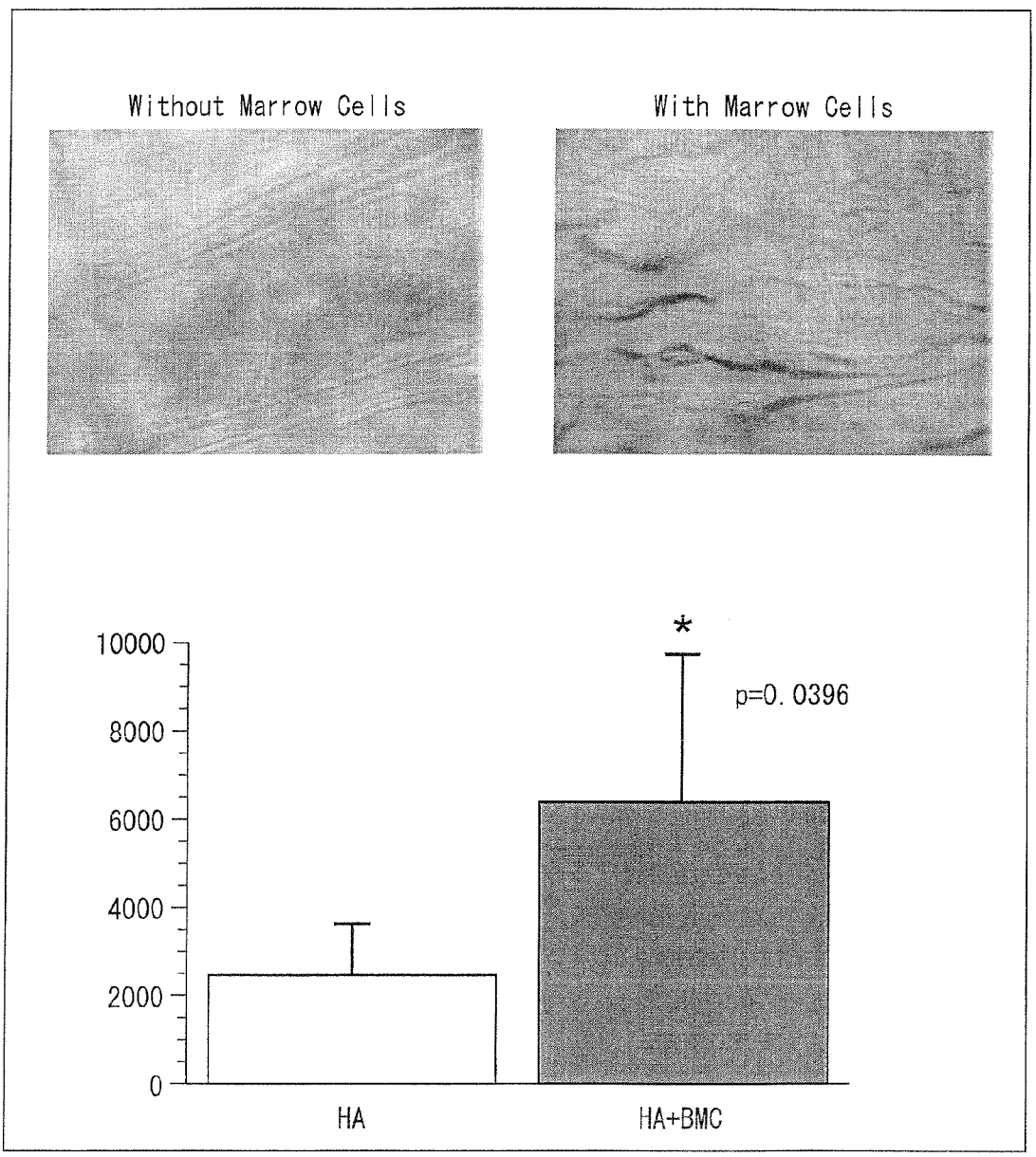

FIG. 7 is a graph illustrating (i) a total length of blood vessels observed in a site to which hydroxyapatite/polylactic acid film/marrow cell complex was administered and (ii) a total length of blood vessels observed in a site to which a hydroxyapatite/polylactic acid film complex was administered.

(a) of FIG. 8 shows photographs of mice each of which has a hind limb to which a corresponding complex based on particulate scaffold was administered. (b) of FIG. 8 is a graph obtained by analyzing a limb survival rate of each of the mice according to a Kaplan-Meier method.

Figure 9:
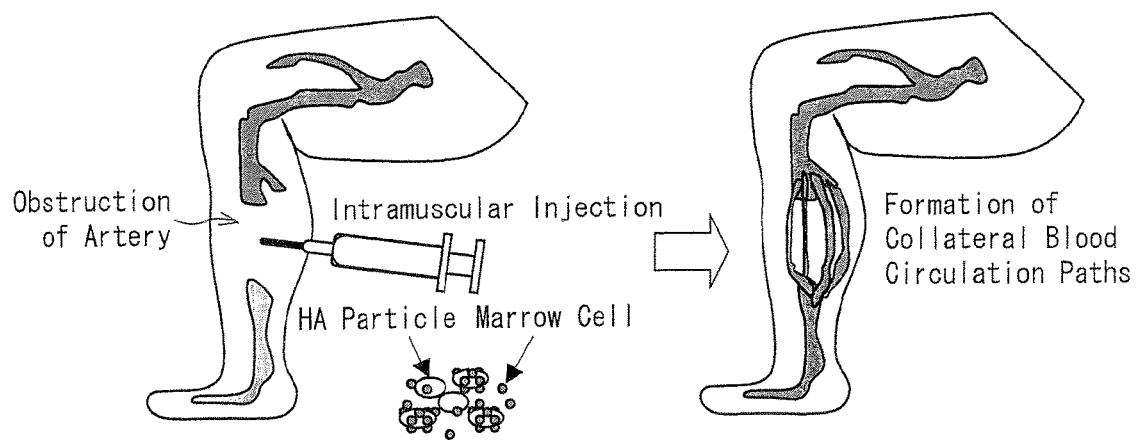

FIG. 9 is a view schematically illustrating an example of how a peripheral arterial disease is treated with use of a medical composition of the present invention.

DESCRIPTION OF EMBODIMENTS

An embodiment of the present invention is described below. Note, however, that the present invention is not limited to this embodiment.

[1. Medical Composition]

A medical composition of the present embodiment includes: a carrier having a support and a surface layer provided on the support; and cells provided on a surface of the carrier. The following description specifically discusses each structure. Note that the medical composition of the present embodiment can be used particularly as a composition for angiogenesis.

[1-1. Support]

The support is made from a bioabsorbable polymer.

The bioabsorbable polymer has a low toxicity to a living subject, and is gradually degraded and absorbed into the living subject. Accordingly, if the support is made from the bioabsorbable polymer, it is possible to keep the medical composition of the present embodiment in the target site in the body until angiogenesis is sufficiently induced. In addition, after angiogenesis is sufficiently induced, the medical composition of the present embodiment can be quickly degraded and absorbed. Further, according to such configuration, the low toxicity to a living subject allow to control side effects such as inflammation.

The bioabsorbable polymer constituting the support is not limited to a particular kind; however, it is preferably at least one selected from the group consisting of: polylactic acid, polyglycolic acid, polyethylene glycol, propylene glycol, polyhydroxybutylate, polycarbonate, polyamide, cellulose, chitin, chitosan, starch, polyglutamic acid, polydioxanone, cyanoacrylate polymers, polycaprolactone, synthetic polypeptides, hyaluronic acid, polymalic acid, poly butylene succinate, and copolymers of any combination of those listed above. Preferable among those is polylactic acid. It is further preferable that the support be made from a combination of polylactic acid and another bioabsorbable polymer. That the support is preferably made solely from polylactic acid, and is more preferably made from a mixture of polylactic acid and another bioabsorbable polymer.

The another bioabsorbable polymer to be used together with polylactic acid is not limited to a particular kind. For example, one of the above-listed bioabsorbable polymers other than polylactic acid can be used, and two or more of the above-listed bioabsorbable polymers other than polylactic acid can be used in combination. Combined use of (i) the another bioabsorbable polymer other than polylactic acid and (ii) polylactic acid makes it possible to achieve a support that is excellent in a biodegrading property, and to control a degradation speed of polylactic acid.

Most preferable examples of the another bioabsorbable polymer used together with polylactic acid encompass: polyglycolic acid; polycaprolactone or polyethylene glycol; and copolymers of any combination of those listed above. According to this configuration, it is possible to increase a degradation speed and an absorption speed of the medical composition of the present embodiment. This makes it possible to improve safety of the medical composition.

The support is not particularly limited as to content of a substance other than polylactic acid in raw materials of the support. For example, in a case where such a substance is polyglycolic acid, the content thereof is preferably 0 wt % to 100 wt % with respect to the raw material, and more preferably 20 wt % to 80 wt % with respect to the raw material. In a case where the substance is polyethylene glycol, the rate of content is also preferably 0 wt % to 100 wt % with respect to the raw material, and more preferably 20 wt % to 80 wt % with respect to the raw material. According to the configuration, it is possible to control, to a desired time period, a time period during which the medical composition of the present embodiment is present in the body.

A shape of the bioabsorbable polymer that constitutes the support, i.e., a shape of the bioabsorbable polymer contained in the support, is not limited to a particular shape, and can be any shape depending on the situation. For example, the bioabsorbable polymer is preferably in a shape of a particle, fiber, film, or nonwoven fabric. Note in the Specification that the "nonwoven fabric" refers to fibers in a form of fabric, which has been formed without a weaving process. Among the shapes listed above, the nonwoven fabric is most preferable. According to this configuration, it is possible to increase a surface area of the support, thereby making it possible to cause a large number of cells to adhere to the support. This makes it possible to more effectively induce angiogenesis. Further, according to the configuration, it is possible to increase, when the medical composition of the present embodiment is administered into a body, an area in which the support and a living subject (e.g., various kinds of enzyme in a bodily fluid) make contact with each other. Accordingly, the medical composition can be quickly degraded and absorbed after exerting its angiogenic effect.

A shape of the support is not limited to a particular kind either, and can be any shape depending on the situation. For example, the support is preferably in a shape of a sphere, film, or flat plate. Among the shapes listed above, the shape of the sphere is most preferable.

The support can have a non-porous structure; however, it preferable that the support have a porous structure (sponge-like structure). Note here that, the support having the porous structure makes it possible to cause a carrier (described later) to also have the porous structure. This makes it possible to increase a surface area of the carrier, thereby making it possible to cause a large number of cells to adhere to the carrier. As a result, it is possible to more effectively induce angiogenesis. Further, it is possible to increase, when the medical composition of the present embodiment is administered into a body, an area in which the support and a living subject (e.g., various kinds of enzyme in a bodily fluid) make contact with each other. Accordingly, the medical composition can be quickly degraded and absorbed after exerting its angiogenic effect.

Size of the support (i.e., a diameter of a cross-sectional surface of the support) is not particularly limited. The support can be configured such that, in a case where the support and a surface layer (described later) constitute a carrier, a particle diameter of the carrier will be preferably 0.01 µm to 5 cm, more preferably 1 µm to 1 mm, and most preferably 10 µm to 200 µm. That is, the size of the support is determined according to a thickness of the later-described surface layer. Note that, if the particle diameter of the carrier is less than 1 mm, then the carrier can be easily administered into a living subject with use of an injector. On the other hand, if the particle diameter of the carrier is 1 mm or greater, the carrier can be administered into a living subject by incision.

[1-2. Surface Layer]

The medical composition of the present embodiment has, on the foregoing support, a surface layer made from hydroxyapatite ($Ca_{10}(PO_4)_6(OH)_2$). The surface layer and the support are main constituents of a carrier (described later), on which cells are provided.

A region, of the support, on which the surface layer is provided is not particularly limited. The surface layer can be provided so as to cover part of a surface of the support, or can be provided so as to cover the entire surface of the support.

A thickness of the surface layer is not particularly limited either. As described earlier, the thickness of the surface layer can be determined so that the particle diameter of the carrier will be preferably 0.01 µm to 5 cm, more preferably 1 µm to 1 mm, and most preferably 10 µm to 200 µm. That is, the thickness of the surface layer is determined according to the size of the foregoing support.

A method of forming the surface layer is not particularly limited. For example, it is preferable to first form nanosized hydroxyapatite particles (i.e., hydroxyapatite nanocrystals), and then coat the support with the nanosized hydroxyapatite particles. Such nanocrystals (particles) can either be an unburned substance (amorphous) or a burned substance.

Size of each of the hydroxyapatite particles with which the support is coated is not particularly limited. For example, a particle diameter of each of the hydroxyapatite particles is preferably 10 nm to 700 nm, more preferably 20 nm to 600 nm, and most preferably 25 nm to 500 nm.

The following description more specifically discusses one example of a method of forming the hydroxyapatite particles (surface layer). In other words, the following description discusses one example of a method of forming the carrier.

The method of forming the surface layer is not particularly limited; however, the method preferably includes at least a "primary particle forming step", a "sintering step", and a "surface layer forming step". The method can further include a "removing step" and a "mixing step". In the following description, a method including all of the above five steps is exemplified as the method of forming the surface layer. Note, however, that the method of forming the surface layer is not limited to this method.

The foregoing five steps are carried out in the order of "1. primary particle forming step", "2. mixing step", "3. sintering step", "4. removing step", and "5. surface layer forming step". The steps 1 through 4 are steps of preparing the hydroxyapatite particles, which constitute the surface layer. The step 5 is a step of forming, on the support, the surface layer constituted by the hydroxyapatite particles, so as to form the carrier that has the support and the surface layer. The following description discusses each of the steps.

<1. Primary Particle Forming Step>

Note here that "primary particles" refers to particles that are formed from hydroxyapatite (HAp), which particles have not yet undergone the sintering step. That is, the "primary particles" refers to particles that are formed for the first time in the course of producing the hydroxyapatite particles. Further, the "primary particles" can be narrowly interpreted as monolithic particles. In the Specification, the "primary particles" can be (i) amorphous particles or (ii) sintered particles made by sintering the amorphous particles.

On the other hand, "secondary particles" refers to a plurality of primary particles that are physically (e.g., through fusion bonding) or chemically (e.g., through ion binding or covalent binding) bound to one another. Note here that the number and shape etc. of the primary particles that are bound to one another are not particularly limited.

In particular, "monocrystal primary particles" refers to primary particles made of hydroxyapatite monocrystals, or to primary particles that are made of the hydroxyapatite monocrystals and aggregate by ionic interaction to form a particle aggregation. As used herein, the "primary particles which aggregate by ionic interaction to from a particle aggregation" refers to a particle aggregation that is formed in such a manner that the primary particles self-aggregate by ionic interaction by being dispersed in water or in a medium containing an organic solvent. Such primary particles do not encompass the secondary particles, which are polycrystalline particles made from particles fused together by sintering.

The primary particle forming step is not limited to a particular kind, as long as the primary particles can be formed. One example of the primary particle forming step is to gradually add, at a high temperature (e.g., 80° C.), a $(NH_4)_2HPO_4$ aqueous solution whose pH has been adjusted to be alkaline (e.g., pH 12.0) into a $Ca(NO_3)_2$ aqueous solution whose pH has been adjusted to be alkaline (e.g., pH 12.0).

Conditions (e.g., particle diameter and particle size distribution) of the primary particles formed in the primary particle forming step will be directly reflected to conditions of the hydroxyapatite particles. Accordingly, in order to produce fine (nanosized) hydroxyapatite particles that are uniform in particle diameter (i.e., the particles with narrow particle size distribution), it is preferable to produce fine (nanosized) primary particles that are uniform in particle diameter (i.e., the particles with narrow particle size distribution) in the primary particle forming step.

The particle diameter of each of the primary particles is not particularly limited; however, the particle diameter is preferably 10 nm to 500 nm, more preferably 20 nm to 450 nm, and most preferably 25 nm to 400 nm. Further, a group of the primary particles has a variation coefficient of particle diameters of preferably less than or equal to 20%, more preferably less than or equal to 18%, and most preferably less than or equal to 15%. Note here that the particle diameter and the variation coefficient of the primary particles can be found by (i) measuring a particle diameter of each of at least 100 primary particles by a dynamic light scattering method or with use of an electron microscope so as to obtain measurement results and (ii) carrying out calculation on the basis of the measurement results. By producing such a group of the primary particles in this step, it will be possible to form a surface layer to which cells (described later) adhere efficiently. Note here that the "variation coefficient" refers to a value that indicates a variation in diameters of particles, and can be found through a formula: Variation Coefficient=Standard Deviation/Average Particle Diameter×100(%).

A method of forming the fine (nanosized) primary particles that are uniform in particle diameter (i.e., the particles with narrow particle size distribution) is not particularly limited. For example, it is possible to employ a method disclosed in Japanese Patent Application Publication, Tokukai, No. 2002-137910 A. Specifically, such primary particles can be synthesized by (i) solubilizing a calcium solution and a phosphoric acid solution so as to mix these solutions into a surfactant/water/oil emulsion phase and (ii) reacting the mixture at a temperature higher than or equal to a cloud point of the surfactant. Note here that the size of each of the primary particles can be controlled by changing (a) functional groups in the surfactant and (b) a ratio of hydrophilicity/hydrophobicity of the surfactant.

The following description briefly discusses a principle of the production method of the above primary particles. In the course of the method for synthesizing hydroxyapatite fine particles by (i) solubilizing a calcium solution and a phosphoric acid solution so as to mix these solutions into a surfactant/water/oil emulsion phase and (ii) reacting the mixture, cores of hydroxyapatite grow into crystals within micelles of the surfactant. Note here that, by setting a reaction temperature to a temperature higher than or equal to a cloud point of the surfactant, it is possible to control thermodynamic stability of the micelles. Specifically, by increasing the reaction temperature to the temperature higher than or equal to a cloud point of the surfactant, it is possible to reduce an ability of the surfactant to form the micelles. As a result, a driving force to promote crystal growth of hydroxyapatite, which force has been restricted by "shackles" of the micelles, becomes greater than a driving force to maintain the micelles serving as the "shackles". By utilizing this mechanism, it is possible to control morphology (e.g., shape and size) of crystals.

Important factors in forming micelles by a surfactant are (i) functional groups (hydrophilic moieties) in the surfactant and (ii) a ratio of hydrophilicity/hydrophobicity of the surfactant. Changing these factors causes a change in stability of the micelles and a cloud point of the surfactant. Further, the cloud point of the surfactant differs depending on types of the surfactant. Therefore, the stability of the micelles and the cloud point of the surfactant can be changed by changing types of the surfactant as needed. This makes it possible to control size of each of the hydroxyapatite fine particles.

The type of the surfactant used in the foregoing method is not limited to a particular type. For example, it is possible to employ a commonly-known anionic surfactant, a commonly-known cationic surfactant, a commonly-known zwitterionic surfactant, or a commonly-known nonionic surfactant, which is disclosed in Japanese Patent Application Publication, Tokukaihei, No. 5-17111 A. More specifically, preferable examples of the nonionic surfactant encompass: polyoxyethylene alkyl ether, polyoxyethylene allyl ether, polyoxyethylene alkyl allyl ether, polyoxyethylene derivative, oxyethylene-oxypropylene block copolymer, sorbitan fatty acid ester, polyoxyethylene sorbitan fatty acid ester, polyoxyethylene sorbitol fatty acid ester, glycerine fatty acid ester, polyoxyethylene fatty acid ester, and polyoxyethylene alkylamine, and the like. Preferable examples of the cationic surfactant encompass: quaternary ammonium salt such as stearylamine hydrochloride, lauryl trimethylammonium chloride, and alkyl benzene dimethyl ammonium chloride; and the like. Preferable examples of the anionic surfactant encompass: fatty alcohol sulfates such as lauryl alcohol sulfuric ester sodium and oleyl alcohol sulfuric ester sodium; alkyl sulfates such as sodium lauryl sulfate and ammonium lauryl sulfate; and alkyl aryl sulfonates such as sodium dodecylbenzenesulfonate and sodium dodecylnaphthalene sulfonate; and the like. Preferable examples of ampholytic surfactant encompass: ampholytic surfactants of the alkyl betaine type, of the alkylamide betaine type, and of the amine oxide type. The surfactant can be used either individually or in a combination of two or more types. Among those surfactants listed above, the most preferable surfactant is pentaethylene glycol dodecyl ether, in view of a cloud point and solubility.

Examples of an oil phase that can be used in the foregoing method encompass: carbon hydrides such as toluene, xylene, hexane, dodecane, and cyclohexane; halogenated hydrocarbons such as chlorobenzene and chloroform; ethers such as diethyl ether; alcohols such as butanol; ketones such as methyl isobutyl ketone and cyclohexanone; and the like.

The oil phase can be used individually or in a combination of two types, depending on the type of the surfactant to be used, so as to have a low solubility of water to the oil phase and to be able to dissolve any of the above-listed surfactants. The most preferable oil phase among those listed above is dodecane, in view of solubility of water and solubility of the surfactant. Other conditions such as a reaction temperature, reaction time, additive amount of raw materials, and the like can be appropriately selected and employed as needed depending on intended composition of the primary particles. Note, however, that an upper limit of the reaction temperature is preferably below a boiling point of the solution. Since the reaction is occurring with an aqueous solution, the upper limit of the reaction temperature is preferably lower than or equal to 90° C.

The primary particle forming step can further include a step of washing the obtained primary particles with water etc., and/or a step of collecting the primary particles by centrifugal separation, filtration, or the like.

<2. Mixing Step>

A mixing step is for mixing the primary particles and an anti-fusion bonding agent. Specifically, the mixing step is for providing, in advance, the anti-fusion bonding agent in gaps between the primary particles included in the group obtained in the primary particle forming step, thereby preventing fusion bonding of the primary particles in the subsequent sintering step. Note here that a mixture of the primary particles and the anti-fusion bonding agent, which mixture is obtained in this mixing step, is hereinafter referred to as "mixed particles".

The anti-fusion bonding agent is not limited to a particular kind, as long as the anti-fusion bonding agent is capable of preventing fusion bonding of the primary particles. However, the anti-fusion bonding agent preferably does not vaporize even at a sintering temperature in the subsequent sintering step. If the anti-fusion bonding agent is nonvolatile under a condition of the sintering temperature, then the anti-fusion bonding agent does not disappear from gaps between the primary particles in the sintering step. This makes it possible to surely prevent fusion bonding of the primary particles. Note, however, that it is not necessary for the anti-fusion bonding agent to be 100% nonvolatile at the sintering temperature, as long as approximately 10% or more of the anti-fusion bonding agent remains in the gaps between the primary particles after completion of the sintering step.

The anti-fusion bonding agent can be chemically decomposed by heat after completion of the sintering step. That is, the anti-fusion bonding agent does not necessarily have to keep being the same substance (compound) before and after the sintering step, as long as the anti-fusion bonding agent remains even after completion of the sintering step.

The anti-fusion bonding agent is preferably soluble in a solvent, particularly in an aqueous solvent. If the anti-fusion bonding agent is soluble in the solvent, it is possible to remove the anti-fusion bonding agent (e.g., calcium carbonate) from the mixed particles, which contains the anti-fusion bonding agent, merely by suspending the mixed particles into the aqueous solvent such as pure water. In particular, in a case where the anti-fusion bonding agent is soluble in the aqueous solvent, it is not necessary to use an organic solvent in removing the anti-fusion bonding agent. This makes it possible to omit, from the removing step, (i) equipment for handing the organic solvent and (ii) organic solvent waste disposal. Accordingly, it is possible to more easily remove the anti-fusion bonding agent from the mixed particles. Note that the solvent is not limited to a particular kind. Examples of the aqueous solvent encompass: water, ethanol, methanol, and the like. Examples of the organic solvent encompass: acetone, toluene, and the like.

The aqueous solvent, for the purpose of increasing solubility of the anti-fusion bonding agent into water, preferably contains: a chelate compound such as oxalate, ethylene diamine, bipyridine, ethylenediamine tetra acetic acid salt, or the like. Further, the aqueous solvent, for the purpose of increasing solubility of the anti-fusion bonding agent into water, preferably contains: electrolytic ion such as sodium chloride, ammonium nitrate, potassium carbonate, or the like.

Note here that, solubility of the anti-fusion bonding agent into the solvent is preferably as high as possible, because the higher solubility allows the anti-fusion bonding agent to be removed more efficiently. In a case where an amount (g) of solute with respect to 100 g of the solvent is referred to as solubility, the solubility of the anti-fusion bonding agent is preferably not less than 0.01 g, more preferably not less than 1 g, and most preferably not less than 10 g.

A specific example of the anti-fusion bonding agent is not particularly limited. Preferable examples of the anti-fusion bonding agent encompass: calcium salt (or complex thereof) such as calcium chlorite, calcium oxide, calcium sulfate, calcium nitrate, calcium carbonate, calcium hydroxide, calcium acetate, and calcium citrate; potassium salt such as calcium polyacrylate, potassium chloride, potassium oxide, potassium sulfate, potassium nitrate, potassium carbonate, potassium hydroxide, and potassium phosphate; sodium salt such as sodium chloride, sodium oxide, sodium sulfate, sodium nitrate, sodium carbonate, sodium hydroxide, and sodium phosphate; and the like.

In the mixing step, a method of mixing the primary particles and the anti-fusion bonding agent is not limited to a particular kind. One example is a method in which hydroxyapatite primary particles in a solid state are mixed with the anti-fusion bonding agent in a solid state, and then the mixture is stirred with use of a blender. Another example is a method in which the primary particles are dispersed into an anti-fusion bonding agent solution. Note however that, since it is difficult to mix solid objects uniformly, the latter method (i.e., the another example) is preferable so as to ensure a state in which the anti-fusion bonding agent is present uniformly in the gaps between the primary particles. In a case of the latter method, it is preferable to dry the anti-fusion bonding agent solution in which the hydroxyapatite primary particles are dispersed. This makes it possible to maintain, over a long period of time, a state in which the hydroxyapatite primary particles and the anti-fusion bonding agent are mixed uniformly.

<3. Sintering Step>

The sintering step is for exposing, to a sintering temperature, the mixed particles obtained in the mixing step so that mixed particles turn into ceramic particles (sintered particles). Note here that, since the anti-fusion bonding agent is present in the gaps between the mixed particles, fusion bonding of the hydroxyapatite primary particles can be prevented even under a condition of a high temperature in the sintering step.

The sintering temperature in the sintering step is not particularly limited, and can be determined so that desired hardness of the ceramic particles will be achieved. For example, the sintering temperature is preferably 100° C. to 1800° C., more preferably 150° C. to 1500° C., and most preferably 200° C. to 1200° C. A sintering time can be determined depending on the desired hardness etc. of the ceramic particles.

Note that an apparatus or the like used for sintering is not particularly limited, and can be any of commercially available firing furnaces.

<4. Removing Step>

The removing step is for removing the anti-fusion bonding agent from gaps between the sintered particles obtained in the sintering step.

Specific means and a method of removing the anti-fusion bonding agent are not particularly limited, and can be determined as needed depending on the anti-fusion bonding agent used in the mixing step. For example, in a case of an anti-fusion bonding agent soluble to a solvent, the anti-fusion bonding agent can be removed by being dissolved into a solvent that dissolves the anti-fusion bonding agent but does not dissolve the hydroxyapatite primary particles.

The solvent used in this process is not limited to a particular kind, as long as the solvent has the foregoing property. The solvent can either be an aqueous solvent or an organic solvent. Note however that, in the removing step, it is preferable to use the aqueous solvent because (i) equipment for handling the organic solvent is not necessary, (ii) equipment for disposing of the organic solvent waste is not necessary, (iii) safety of producing operation is high, (iv) risks to the environment are low, and (v) the like.

Preferable examples of the aqueous solvent encompass: water, ethanol, methanol, and the like. Preferable examples of the organic solvent encompass: acetone, toluene, and the like.

The aqueous solvent, for the purpose of increasing solubility of the anti-fusion bonding agent, preferably contains: a chelate compound such as oxalate, ethylene diamine, bipyridine, ethylenediamine tetra acetic acid salt, or the like. Further, the aqueous solvent, for the purpose of increasing solubility of the anti-fusion bonding agent, preferably contains: electrolytic ion such as sodium chloride, ammonium nitrate, potassium carbonate, or the like.

Further, the removing step is preferably carried out under a condition of pH 4.0 to pH 12.0, because the sintered particles made from hydroxyapatite (HAp) are dissolved under a condition of pH 4.0 or less.

In a case of using the solvent so as to remove the anti-fusion bonding agent, the removing step can be carried out by (i) suspending, into the solvent, a group of the sintered particles which group was obtained in the sintering step and contains the anti-fusion bonding agent, and thereafter (ii) collecting only hydroxyapatite particles by filtration or centrifugal separation. In a production method of the hydroxyapatite particles, the number of times of the removing step is not limited to one, and can be two or more. With a plurality of removing steps, more anti-fusion bonding agent can be removed from gaps between the hydroxyapatite particles.

Besides the foregoing method of removing the anti-fusion bonding agent with use of the solvent, there is another method of removing the anti-fusion bonding agent. Specifically, by using an anti-fusion bonding agent made of a magnetic material, it is possible to remove the anti-fusion bonding agent with use of a magnet. More specifically, the anti-fusion bonding agent can be removed by (i) suspending, into a certain solvent (e.g., water), a group of the sintered particles which group was obtained in the sintering step and contains the anti-fusion bonding agent, so as to disperse the sintered particles into the solvent, (ii) magnetizing the obtained suspension solution so that only the anti-fusion bonding agent is attracted by the magnet, and then (iii) collecting only the hydroxyapatite particles which had not been attracted by the magnet. Alternatively, the anti-fusion bonding agent can be removed by (a) grinding the sintered particles to powder without suspending the sintered particles into the solvent and then (b) separating the anti-fusion bonding agent with use of the magnet.

It is preferable that the removing step further include a classifying step so as to make particle diameters of the hydroxyapatite particles uniform. The classifying step is not particularly limited, as long as the particle diameters of the hydroxyapatite particles can be made uniform. For example, classification can be carried out by filtration or centrifugal separation; however, the classifying step is not limited to these methods.

In this way, the hydroxyapatite particles for coating a surface of the support can be prepared.

<5. Surface Layer Forming Step>

The surface layer forming step is for coating the support with the hydroxyapatite particles obtained through the foregoing series of steps, thereby forming the surface layer on the support. In other words, the surface layer forming step is to form a carrier that has a support and a surface layer.

The surface layer forming step is not particularly limited in its specific configuration, as long as the step is capable of forming the surface layer on the support so as to form the carrier having the support and the surface layer. For example, in the surface layer forming step, the hydroxyapatite particles are dissolved in a certain solvent so as to give a solution, and thereafter the support is dispersed into the solution.

The solvent is not limited to a particular kind. For example, the solvent can be an aqueous solvent or an organic solvent. More specifically, preferable examples of the aqueous solvent encompass: water, ethanol, methanol, and the like. Preferable examples of the organic solvent encompass: acetone, toluene, and the like.

The solvent containing the hydroxyapatite particles and the support is preferably subjected to supersonic treatment. The supersonic treatment makes it possible to form the surface layer, with a more uniform thickness, over the entire surface of the support. Specific conditions of the supersonic treatment are not particularly limited. Further, a device for carrying out the supersonic treatment can be any of commonly available devices.

It is preferable that the surface layer forming step include, after the ultrasonic treatment, steps of separating and washing the support coated with the hydroxyapatite particles (i.a carrier) and then drying the carrier.

A step of separating the carrier is not particularly limited. For example, the carrier is preferably separated by centrifugal separation or filtration. Further, such a carrier can be washed with a solvent. The solvent is not limited to a particular kind. For example, the solvent is preferably an aqueous solvent or an organic solvent. More specifically, preferable examples of the aqueous solvent encompass: water, ethanol, methanol, and the like. Preferable examples of the organic solvent encompass: acetone, toluene, and the like.

The carrier is preferably dried after being washed. A method of drying the carrier is not particularly limited. For example, the carrier can be dried at a room temperature, and can be dried by controlling a temperature to a desired temperature.

In this way, it is possible to prepare a carrier, on which cells (described later) are provided.

Note here that the carrier formed through the foregoing step is in a particle form. In the Specification, the term "in a particle form" intends to fine particle(s), which has size and shape suitable for administration using an injector. The shapes of such fine particles are not particularly limited; however, the shapes are preferably spheres, rods, needles, scales, fabrics, sheets, or any combination thereof.

Specifically, a particle diameter of the carrier is preferably 0.01 µm to 5 cm, and more preferably 1 µm to 1 mm. If the particle diameter of the carrier is less than 10 µm, then there is a tendency that the medical composition of the present embodiment easily enter a blood capillary. On the other hand, if the particle diameter of the carrier is greater than 200 µm, then the medical composition become easy to aggregate. In other words, if the particle diameter of the carrier is greater than 200 µm, then the medical composition likely clogs in an injection needle when being administered into a living subject with use of the injector. For these reasons, the particle diameter of the carrier is most preferably 10 µm to 200 µm. Note that, if the particle diameter of the carrier is less than or equal to 1 mm, then the carrier can be easily administered into a living subject with use of the injector. On the other hand, if the particle diameter of the carrier is 1 mm or greater, then the carrier can be administered into a living subject by incision.

The particle diameter of the carrier can be measured by a commonly known method. For example, the particle diameter can be measured, by a dynamic light scattering method or with use of an electron microscope, in a similar manner to the foregoing primary particles.

[1-3. Cells]

As described so far, according to the medical composition of the present embodiment, cells are provided on the carrier prepared through the foregoing steps.

The cells are not limited to a particular kind, as long as the cells are capable of inducing angiogenesis. For example, the cells are preferably selected from the group consisting of: myelomonocytic cells, peripheral-blood mononuclear cells, multipotent stem cells, hematopoietic stem cells, vascular endothelium precursor cells, iPS cells, ES cells, platelet, and mesenchymal stem cells. More preferable among those are myelomonocytic cells, peripheral-blood mononuclear cells, multipotent stem cells, hematopoietic stem cells, and vascular endothelium precursor cells, because these cells have already been demonstrated in a human or animal to be effective in angiogenesis therapy. Further, in view of a source of the cells, iPS cells and ES cells are more preferable because these cells do not place a burden on a body of a patient.

A method of providing the cells on the surface of the carrier is not particularly limited. For example, the cells are preferably provided on the surface of the carrier through interaction between the cells and the surface layer. The interaction is not limited to a particular kind. For example, the cells can be (i) immobilized on the carrier with use of a cross-linking agent, (ii) caused to adhere to the carrier by adhesive ability of the cells, (iii) adsorbed to the carrier by adsorptive ability of hydroxyapatite, or (iv) immobilized on the carrier by a combination of any of (i) through (iii). The cross-linking agent is not limited to a particular kind, and can be any of commonly-known cross-linking agents. The cells can be provided directly on the surface of the carrier, and can be provided indirectly on the surface of the carrier via other cells. Specifically, it is also possible to provide a cell aggregation, which is composed of many cells, on the carrier by immobilizing some of these cells on the carrier.

Further, in a case where the carrier has a porous structure, the cells can be provided also in pores of the porous structure.

A specific method of immobilizing the cells onto the carrier is not particularly limited. For example, it is preferable to mix the carrier and the cells, and more preferably to culture the cells on the carrier for a certain period of time. In a case of culturing the cells, a time period over which the cells are cultured is not particularly limited. For example, the time period is preferably 0.1 to 24 hours. By culturing the cells for a period within the above range, it is possible to cause the cells to more firmly adhere to the carrier. In addition, by culturing the cells for a period within the above range, it is possible to proliferate the cells adhering to the carrier. This makes it possible to enhance angiogenic effect of the medical composition of the present embodiment.

A ratio of the carrier to the cells provided on the carrier is not particularly limited. For example, the ratio by weight is preferably 1/10 to 10/1. In a case where the ratio by weight is greater than or equal to 1/10, i.e., in a case where a sufficient amount of cells are provided on the carrier, it is possible to effectively generate new blood vessels. In addition, in a case where the ratio by weight is less than or equal to 10/1, it is possible not only to effectively generate new blood vessels, but also to surely prevent side effects (e.g., inflammation) of hydroxyapatite etc. which may occur to a living subject.

The medical composition of the present embodiment preferably contains, in addition to the cells, any biologically active substance provided on the surface of the carrier.

The biologically active substance is not limited to a particular kind. For example, the biologically active substance is preferably at least one selected from the group consisting of: an anti-inflammatory agent, angiogenesis cytokine, antibiotic, and a cell growth factor. For example, in a case where the angiogenesis cytokine is provided on the carrier, it is possible to more effectively induce angiogenesis. In a case where the anti-inflammatory agent is provided on the carrier, it is possible to prevent occurrence of inflammation even if a large amount of medical composition is administered into a living subject. In a case where antibiotic is provided on the carrier, it is possible to prevent various secondary infections etc. In a case where the cell growth factor is provided on the carrier, it is possible not only to induce angiogenesis, but also to regenerate various types of cells (various types of tissues) if needed.

The angiogenesis cytokine is not limited to a particular kind. For example, the angiogenesis cytokine is preferably at least one selected from the group consisting of: aFGF (acidic fibroblast growth factor), bFGF (basic fibroblast growth factor), VEGF (vascular endothelial growth factor), HGF (hepatocyte growth factor), PDGF (platelet-derived growth factor), PlGF (platelet-induced growth factor), TNF (tumor necrosis factor), EGF (epidermal growth factor), angiopoietin, IL (interleukin), HAPO (hemangiopoietin), Shh (sonic hedgehog), TGF-β (transforming growth factor-beta), G-CSF (granulocyte-colony stimulating factor), M-CSF (macrophage-colony stimulating factor), SCF (stem cell factor), EPO (erythropoietin), TPO (thrombopoietin), and Flt (FMS-like tyrosine kinase ligand). According to this configuration, it is possible to induce angiogenesis more effectively as compared to the case where the cells alone are provided on the carrier.

A method of providing the biologically active substance on the surface of the carrier is not particularly limited. For example, the biologically active substance is provided onto the carrier preferably by interaction between the cells and the surface layer. The interaction is not limited to a particular kind. For example, the biologically active substance can be (i) immobilized on the carrier with use of a cross-linking agent, (ii) adsorbed to the carrier by adsorptive ability of hydroxyapatite, or (iii) immobilized on the carrier by a combination of (i) and (ii). The cross-linking agent is not limited to a particular kind, and can be any of commonly known cross-linking agents.

[2. Medical Kit]

A medical kit of the present embodiment includes: the foregoing medical composition in accordance with the present invention; and an injector for administering the medical composition to a living subject (e.g., a body of a patient). The medical kit of the present embodiment can be used particularly as a kit for angiogenesis.

Since the medical composition has been described already, description for the medical composition is omitted here.

The injector is not limited to a particular kind, as long as the injector is capable of administering, via its needle, the medical composition into a living subject. Examples of the injector encompass not only a commonly used injector, but also a catheter, an instillator, and the like.

The medical kit of the present embodiment can include an additional component(s) of various kinds if needed, in addition to the injector. The additional component is not limited to a particular kind. For example, the additional component is preferably at least one selected from the group consisting of: an injection needle, disinfectant, a drape, and a knife. According to a medical kit further including the additional component, it is possible to more readily and safely administer the medical composition of the present invention into a living subject.

According to the medical kit of the present embodiment, it is possible to administer the medical composition into a living subject with use of the injector. That is, it is possible for a patient himself to easily administer the medical composition to a local site.

The medical kit of the present embodiment preferably includes a liquid that can be used as an injection solution. The liquid can be any liquid as long as it is capable of dissolving the medical composition of the present invention and has a low toxicity to a living subject. One example of the liquid is physiologic saline; however, the liquid is not limited to the physiologic saline.

[3. Production Method of Medical Composition]

A production method of the medical composition of the present embodiment is a method including a step of mixing (i) cells and (ii) a carrier in a particle form, which carrier has (a) a support made from a bioabsorbable polymer and (b) a surface layer provided on the support and made from hydroxyapatite.

Note here that, since specific configurations of the bioabsorbable polymer, support, surface layer, carrier, and cells have already been described earlier, descriptions therefor are omitted here.

In this step, the carrier and the cells are mixed with one another, thereby providing the cells to a surface of the carrier. The cells can be provided directly on the surface of the carrier, and can be provided indirectly on the surface of the carrier via other cells.

A specific method of carrying out this step is not particularly limited. For example, the carrier and the cells can be mixed in a liquid (e.g., a liquid culture medium, physiologic saline, or a buffer such as a phosphoric acid buffer).

In this step of mixing the carrier and the cells, the number, per carrier, of the cells to be mixed is preferably less than or equal to $1 \times 10^{10}$, more preferably less than or equal to $1 \times 10^{8}$, further preferably less than or equal to $1 \times 10^{6}$, and most preferably less than or equal to $1 \times 10^{4}$. According to this configuration, it is possible not only to suitably induce angiogenesis, but also to suppress occurrence of side effects such as inflammation.

Note that, the medical composition produced through the production method of the present embodiment, i.e., the medical composition of the present invention, encompasses also a liquid in which the carrier and the cells are mixed with one another in the step of mixing. That is, in the medical composition of the present invention, some of the cells may not be adhering directly to the carrier.

EXAMPLES

In order to study angiogenic effect of the medical composition of the present invention in a simple manner, both of a first configuration employing a polylactic acid film and a second configuration employing polylactic acid particles were studied in the following examples. The first configuration and the second configuration achieved an equivalent effect of angiogenesis. However, the second configuration was superior to the first configuration in view of easiness of administration, scars left by the administration, the necessity of treatment of the scars, and the like. This will be easily understood from the following specific description.

[1. Preparation of Hydroxyapatite Particles]

A $Ca(NO_3)_2$ aqueous solution (42 mN, 800 mL), whose pH had been adjusted to 12.0 with ammonia water, was poured into a 1 L flask in which a condenser and a semilunar stirring blade were provided. Then, the mixture was kept at 80° C.

A $(NH_4)_2HPO_4$ aqueous solution (100 mN, 200 mL), whose pH had been adjusted to 12.0 with ammonia water, was added to the flask at a temperature of 80° C. and a rate of 10 mL/h. Then, the mixture was reacted for 24 hours. In this way, hydroxyapatite primary particles were prepared.

Into 100 mL of aqueous solution (pH 12.0) containing 1.0 g of polyacrylic acid (manufactured by ALDRICH, weight-average molecular weight: 15,000 g/mol), 1.0 g of the hydroxyapatite primary particles were dispersed so as to adsorb polyacrylic acid to surfaces of the hydroxyapatite primary particles. This process is more specifically described below.

First, 1.0 g of polyacrylic acid (manufactured by ALDRICH, weight-average molecular weight: 15,000 g/mol) was dissolved into 100 mL of pure water so as to obtain a polyacrylic acid aqueous solution. Next, pH of the polyacrylic acid aqueous solution was adjusted to 12.0 by adding an ammonia aqueous solution (25% aqueous solution) with stirring at a room temperature. The pH of the polyacrylic acid aqueous solution was measured with use of a pH meter D-24SE (manufactured by HORIBA, Ltd.). Then, 1.0 g of the hydroxyapatite primary particles were dispersed into 100 mL of the polyacrylic acid aqueous solution so as to obtain a dispersion solution. Thereafter, 100 mL of calcium nitrate ($Ca(NO_3)_2$) aqueous solution (0.12 mol/L) was added to the dispersion solution. In this way, calcium polyacrylate was separated out on the surfaces of the hydroxyapatite primary particles. Note here that the obtained calcium polyacrylate serves as an anti-fusion bonding agent.

Then, the resultant precipitates were collected, and dried under a reduced pressure (approximately 0.1 Pa) at 80° C. In this way, mixed particles were obtained.

The mixed particles were placed in a crucible, and baked for an hour at a sintering temperature of 800° C. so as to obtain sintered particles. In this process, the calcium polyacrylate was pyrolyzed and turned into calcium oxide (CaO).

Note here that, at the completion of this sintering step, a residual ratio of calcium oxide (CaO) was not less than 25%.

Then, the sintered particles obtained in the sintering step were suspended into 500 mL of 50 mmol/L ammonium nitrate ($NH_4NO_3$) aqueous solution. Thereafter, the sintered particles were separated by centrifugal separation and then washed. Further, the sintered particles were suspended in distilled water, and thereafter separated and washed in the same manner as above. In this way, the anti-fusion bonding agent and ammonium nitrate were removed, so as to collect the hydroxyapatite particles (hydroxyapatite nanocrystals).

Next, particle diameters of the hydroxyapatite particles were measured by a dynamic light scattering method. The dynamic light scattering was measured with use of Dynamic Light Scattering Spectrophotometer DLS-6000 (manufactured by Otsuka Electronics. Ltd.) at a room temperature under a condition where a particle concentration was 10 ppm and a scattering angle was 90 degrees. As a result, it was found that the particle diameters ranged from 60 nm to 100 nm, and a variation coefficient of the particle diameters was as low as 11%. This demonstrated that the nanocrystals were particles that had uniform particle diameters (i.e., the particle with narrow particle size distribution).

[2. Preparation of Hydroxyapatite/Polylactic Acid Film Complex]

A polylactic acid nonwoven fabric film (thickness: 140 µm, fiber density: 20 g/m$^2$, tear strength: 3N) was immersed in an ammonia aqueous solution (pH 12.0) for 30 minutes, thereby introducing carboxyl groups into a surface of the polylactic acid nonwoven fabric film. Then, the resultant polylactic acid particles were washed with water and ethanol.

The hydroxyapatite particles prepared in Example 1 were dispersed into ethanol so that concentration of the resulting dispersion solution would be 2 wt %.

The polylactic acid nonwoven fabric film thus washed was immersed in the dispersion solution, in which the hydroxyapatite particles were dispersed. Then, the dispersion solution was subjected to ultrasonic irradiation (ultrasonic irradiator: US-2 manufactured by NND Ltd., Power: 120 W, Frequency: 38 kHz) for 5 minutes at a room temperature. Then, after the dispersion solution was allowed to stand for 30 minutes at a room temperature, the polylactic acid nonwoven fabric film was washed with ethanol, and then dried at a room temperature.

The obtained hydroxyapatite/polylactic acid film complex was observed under a scanning electron microscope, and found that a surface of the polylactic acid film was uniformly coated with the hydroxyapatite particles. Approximately 40% of the surface of the polylactic acid film was coated with the hydroxyapatite particles. Note here that the hydroxyapatite/polylactic acid film complex was observed with use of a scanning electron microscope JSM-6301F (manufactured by JEOL Ltd.) at 90,000-fold magnification.

[3. Preparation of Hydroxyapatite/Polylactic Acid Particle Complex]

Polylactic acid particles (particle diameter: 100 µm) were washed with ethanol at a room temperature. Next, the hydroxyapatite particles prepared in Example 1 were dispersed into ethanol so that concentration of the resulting solution would be 2 wt %.

The polylactic acid particles thus washed were immersed into the ethanol in which the hydroxyapatite particles are dispersed. Then, the dispersion solution was subjected to ultrasonic irradiation (ultrasonic irradiator: US-2 manufactured by NND Ltd., Power: 120 W, Frequency: 38 kHz) for 5 minutes at a room temperature. Then, after the dispersion solution was allowed to stand for 30 minutes at a room temperature, the polylactic acid particles were washed with ethanol, and then dried at a room temperature.

The obtained hydroxyapatite/polylactic acid particle complexes were observed under a scanning electron microscope, and found that a surface of each of the polylactic acid particles was uniformly coated with the hydroxyapatite nanocrystals. Approximately 100% of the surface of each of the polylactic acid particles was coated with the hydroxyapatite particles. Note here that the hydroxyapatite/polylactic acid particle complexes were observed with use of a scanning electron microscope JSM-6301F (manufactured by JEOL Ltd.) at 90,000-fold magnification.

[4. Adhesion Property of Marrow Cells to Hydroxyapatite/Polylactic Acid Film Complex]

On (i) the hydroxyapatite/polylactic acid film complex prepared in Example 2 and (ii) on the hydroxyapatite/polylactic acid particle complexes prepared in Example 3, marrow cells were cultured for 2.5 hours. Note here that (a) a polylactic acid film having no hydroxyapatite particle or (b) polylactic acid particles having no hydroxyapatite particle was/were used as a control.

After the marrow cells were cultured, the marrow cells adhering to the hydroxyapatite/polylactic acid film complex and the marrow cells adhering to the hydroxiapatite/polylactic acid particle complexes were fixed in a phosphate buffer/glutaraldehyde. Thereafter, the obtained hydroxyapatite/polylactic acid film/marrow cell complex was sequentially immersed into a 50% ethanol aqueous solution and then into a 100% ethanol aqueous solution so as to be dehydrated.

Then, the obtained hydroxyapatite/polylactic acid film/marrow cell complex and hydroxyapatite/polylactic acid particle/marrow cell complexes were treated with butanol and then freeze-dried. Thereafter, the hydroxyapatite/polylactic acid film/marrow cell complex and the hydroxyapatite/polylactic acid particle/marrow cell complexes were observed under a scanning electron microscope. (a) of FIG. 1 shows a result for the polylactic acid particles, and (b) of FIG. 1 shows a result for the hydroxyapatite/polylactic acid particles. On the other hand, (c) of FIG. 1 shows a result for the polylactic acid film, and (d) of FIG. 1 shows a result for the hydroxyapatite/polylactic acid film.

As is clear from (a) and (c) of FIG. 1, no marrow cell was observed on the polylactic acid particles having no hydroxyapatite particle and on the polylactic film having no hydroxyapatite particle. In contrast, as is clear from (b) and (d) of FIG. 1, a large number of marrow cells in a form of particles were observed on the hydroxyapatite/polylactic acid particle complexes and on the hydroxyapatite/polylactic acid film complex. Note here that the hydroxyapatite/polylactic acid film/marrow cell complex was observed with use of a scanning electron microscope JSM-6301F (manufactured by JEOL Ltd.) at 300-fold magnification.

Meanwhile, on the hydroxyapatite/polylactic acid film complex prepared in Example 2, L929 cells were cultured for 6 days. Note here that a polylactic acid film not coated with the hydroxiapatite particles was used as a negative control.

After the L929 cells were cultured for 6 days, each of the obtained hydroxyapatite/polylactic acid film/L929 cell complex and polylactic acid film/L929 cell complex was treated with trypsin. Thereafter, an adhesion state of the L929 cells was observed under a light microscope.

(a) of FIG. 2 shows the polylactic acid film/L929 cell complex which has not yet been treated with trypsin. (b) of FIG. 2 shows the polylactic acid film/L929 cell complex which has been treated with trypsin. Further, (c) of FIG. 2 shows the hydroxyapatite/polylactic acid film/L929 cell complex which has not yet been treated with trypsin. (d) of FIG. 2 shows the hydroxyapatite/polylactic acid film/L929 cell complex which has been treated with trypsin.

As is clear from (a) through (d) of FIG. 2, it was found that the L929 cells easily fell off from the polylactic acid film not coated with the hydroxyapatite particles, whereas the L929 cells do not easily fall off from the polylactic acid film coated with the hydroxyapatite particles. That is, it was found that cells on a nanoscaffold coated with the hydroxyapatite particles firmly adhered to the nanoscaffold, and thus did not easily fall off even through trypsin treatment.

[5. Adhesion Property of Marrow Cells to Hydroxyapatite/Polylactic Acid Particle Complex]

On the hydroxyapatite/polylactic acid particle complexes prepared in Example 3, marrow cells were cultured for 2.5 hours.

After the marrow cells were cultured, the marrow cells adhering to the hydroxyapatite/polylactic acid particle complexes were fixed in a phosphate buffer/glutaraldehyde. Thereafter, the obtained hydroxyapatite/polylactic acid particle/marrow cell complexes were sequentially immersed into a 50% ethanol aqueous solution and then into a 100% ethanol aqueous solution so as to be dehydrated.

Then, the hydroxyapatite/polylactic acid particle/marrow cell complexes were treated with butanol and then freeze-dried. Thereafter, the resultant hydroxyapatite/polylactic acid particle/marrow cell complexes were observed under a scanning electron microscope. As a result, as is the case with the hydroxyapatite/polylactic acid film complex, a large number of marrow cells in a form of particles were observed on the hydroxyapatite/polylactic acid particle complexes. Note here that the hydroxyapatite/polylactic acid particle/marrow cell complexes were observed with use of a scanning electron microscope JSM-6301F (manufactured by JEOL Ltd.) at 300-fold magnification.

[6. Angiogenesis Enhancing Effect of Hydroxyapatite/Polylactic Acid Film/Marrow Cell Complex]

First, mice with hind limb ischemia were prepared by commonly-known femoral artery excision. Then, each of the hydroxyapatite/polylactic acid film/marrow cell complex in a form of a film and the hydroxyapatite/polylactic acid film complex was attached to a surface of a muscle of the hind limb, of a corresponding one of the mice, in which the femoral artery was excised. Then, skin of the mouse was sutured (see (a) of FIG. 3). Further, each of (i) the hydroxyapatite/polylactic acid particle/marrow cell complexes in a particle form and (ii) the hydroxyapatite/polylactic acid particle complexes were administered into a muscle of a corresponding one of the mice with use of an injector (see (b) of FIG. 3). After two weeks from the administration, the mice were analyzed with use of a scanning microscope for evidence of angiogenesis.

Specifically, after two weeks from the administration, the administration sites were incised so as to be observed. In his way, it was confirmed that each of the hydroxyapatite/polylactic acid film/marrow cell complex and the hydroxyapatite/polylactic acid film complex was administered under tissues.

Next, the analysis was carried out for evidence of angiogenesis. As a result, it was found that, in a case where the hydroxyapatite/polylactic acid particle/marrow cell complexes or the hydroxyapatite/polylactic acid film/marrow cell complex were/was administered, a large number of new blood vessels were generated in the vicinity of a surface of each of the hydroxyapatite/polylactic acid particle/marrow cell complexes or the hydroxyapatite/polylactic acid film/marrow cell complex (see (a) through (c) of FIG. 4). Specifically, a region indicated by a dotted line in each of (a) and (b) of FIG. 4 is a site to which the hydroxyapatite/polylactic acid particle/marrow cell complexes or the hydroxyapatite/polylactic acid film/marrow cell complex were/was administered. It was found that, in this site, a large number of new blood vessels were generated. Note that (c) of FIG. 4 is an enlarged photograph of the site in which angiogenesis is occurring.

On the other hand, FIG. 5 is a photomicrograph of the site to which the hydroxyapatite/polylactic acid particle complexes or the hydroxyapatite/polylactic acid film complex were/was administered. In the site to which the hydroxyapatite/polylactic acid film complex was administered, no angiogenesis was observed.

Also through observation with use of a stereoscopic microscope, it was found that, in a case where the hydroxyapatite/polylactic acid particle/marrow cell complexes or the hydroxyapatite/polylactic acid film/marrow cell complex were/was administered, a large number of new blood vessels were generated inside and outside of the hydroxyapatite/polylactic acid particle/marrow cell complexes or the hydroxyapatite/polylactic acid film/marrow cell complex. For example, (c) of FIG. 6 is a photomicrograph of the site to which the hydroxyapatite/polylactic acid film/marrow cell complex was administered. As is clear from (c) of FIG. 6, angiogenesis was observed in this site. (d) of FIG. 6 is a photomicrograph, which focuses on the administered hydroxyapatite/polylactic acid film/marrow cell complex. In (d) of FIG. 6, the marrow cells are indicated by white arrows. That is, it was confirmed that, in a case where the hydroxyapatite/polylactic acid film/marrow cell complex was administered, the marrow cells adhering to the hydroxyapatite/polylactic acid film complex remained on the surface of the hydroxyapatite/polylactic acid film complex even after two weeks from the transplantation.

On the other hand, in a case where the hydroxyapatite/polylactic acid film complex was administered, no angiogenesis was observed in the vicinity of the complex (see (a) of FIG. 6). Further, in this case, no marrow cells were observed in the vicinity of the complex (see (b) of FIG. 6).

As is clear from the above results, the hydroxyapatite/polylactic acid film/marrow cell complex and the hydroxyapatite/polylactic acid particle/marrow cell complexes have a strong angiogenic effect, and are capable of holding cells (e.g., marrow cells) adhering thereto alive over a long period of time.

Moreover, a total length of blood vessels observed in each of (i) the site to which the hydroxyapatite/polylactic acid film/marrow cell complex was administered and (ii) the site to which the hydroxyapatite/polylactic acid film complex was administered was measured with use of a microscope. As shown in FIG. 7, (a) the total length of the blood vessels in the site to which the hydroxyapatite/polylactic acid film/marrow cell complex was administered was approximately three times (b) the total length of the blood vessels in the site to which the hydroxyapatite/polylactic acid film complex was administered. This also demonstrated that the hydroxyapatite/polylactic acid film/marrow cell complex induced angiogenesis.

The hydroxyapatite/polylactic acid particle/marrow cell complexes and the hydroxyapatite/polylactic acid film/marrow cell complex exerted substantially the same level of angiogenic effect. However, the hydroxyapatite/polylactic acid particle/marrow cell complexes were superior in view of easiness of administration, scars left by the administration, the necessity of treatment of the scars, and the like. Under such circumstances, the effect of the hydroxyapatite/polylactic acid particle/marrow cell complexes was more specifically studied.

[7. Angiogenesis Enhancing Effect of Hydroxyapatite/Polylactic Acid Particle/Marrow Cell Complex]

First, limb ischemia was induced in BALB/C mice by a commonly know method. Then, each of (i) the hydroxyapatite/polylactic acid particle/marrow cell complexes, the hydroxyapatite/polylactic acid particle complexes, and (iii) marrow cells alone, were administered with use of an injector into a muscle of a hind limb, of a corresponding one of the mice, in which femoral artery was excised. Thereafter, prognosis of the hind limb ischemia was observed. Note here that the marrow cells were obtained from another BALB/C mouse other than the BALB/C mice used in this experiment.

As shown in (a) of FIG. 8, it was observed that, in a case of the mouse to which the hydroxyapatite/polylactic acid particle complexes or the marrow cells alone were administered, the mouse's hind limb was lost or became necrotic. In contrast, it was observed that, in a case of the mouse to which the hydroxyapatite/polylactic acid particle/marrow cell complexes were administered, the mouse's hind limb recovered. (b) of FIG. 8 shows the results of detailed analysis, of a limb survival rate of the mice, which was carried out according to a Kaplan-Meier method. The results shown in (b) of FIG. 8 also demonstrated that the mouse to which the hydroxyapatite/polylactic acid particle/marrow cell complexes were administered was cured of its hind limb ischemia.

The invention is not limited to the description of the embodiments above, but may be altered within the scope of the claims. An embodiment based on a proper combination of technical means disclosed in different embodiments is encompassed in the technical scope of the invention.

INDUSTRIAL APPLICABILITY

A medical composition in accordance with the present invention makes it possible not only to regenerate damaged blood vessels in tissues, but also to generate new blood vessels in desired tissues. Accordingly, the medical composition in accordance with the present invention can be used for treatment of peripheral arterial disease (e.g., arteriosclerosis obliterans, Buerger's disease [Burger's disease], collagenosis, Raynaud's disease, and the like) or for treatment of intractable ulcer (e.g. bedsores, diabetic foot, collagenosis, ischemic ulcer, and the like) (for example, see FIG. 9). Further, the present invention makes it possible to provide a medical composition intended to be administered with use of an injector. Moreover, the medical composition and a medical kit in accordance with the present invention can be used particularly as a composition for angiogenesis (composition for revascularization) and a kit for angiogenesis (kit for revascularization), respectively.

The invention claimed is:

1. A medical composition for injection, the composition comprising:
    a carrier in particle form, the carrier having (i) a support made from a bioabsorbable polymer particle and (ii) a surface layer made from hydroxyapatite nanocrystal particles, which have diameters of 25 nm to 500 nm, and provided on the support, wherein the particle diameter of the carrier is not less than 10 μm and not greater than 200 μm; and
    a sufficient number of cells, which are effective to generate new blood vessels in a living subject, said cells being adhered directly onto the surface layer of the carrier by adhesive ability of said cells by mixing said carrier and said cells in such a manner that the number, per carrier, of said cells to be mixed is less than or equal to $1 \times 10^{10}$;
    wherein the composition does not contain gelatin,
    wherein the ratio by weight of said carrier to said cells is from 1/10 to 10/1, and
    wherein said cells are myelomonocytic cells.

2. The medical composition according to claim 1, wherein the carrier has a porous structure.

3. The medical composition according to claim 1, wherein the bioabsorbable polymer is at least one selected from the group consisting of: polylactic acid, polyglycolic acid, polyethylene glycol, propylene glycol, polyhydroxybutylate, polycarbonate, polyamide, cellulose, chitin, chitosan, starch, polyglutamic acid, polydioxanone, cyanoacrylate polymers, polycaprolactone, synthetic polypeptides, hyaluronic acid, polymalic acid, poly butylene succinate, and copolymers of any combination thereof.

4. The medical composition according to claim 1, further comprising angiogenesis cytokine provided on the surface of the carrier.

5. The medical composition according to claim 4, wherein the angiogenesis cytokine is at least one selected from the group consisting of: acidic fibroblast growth factor, basic fibroblast growth factor, vascular endothelial growth factor, hepatocyte growth factor, platelet-derived growth factor, platelet-induced growth factor, tumor necrosis factor, epidermal growth factor, angiopoietin, interleukin, hemangiopoietin, sonic hedgehog, transforming growth factor-beta, granulocyte-colony stimulating factor, macrophage-colony stimulating factor, stem cell factor, erythropoietin, thrombopoietin, and FMS-like tyrosine kinase ligand.

6. A medical kit, comprising:
    a medical composition recited in claim 1; and
    an injector for administering the medical composition to a living subject.

7. The medical composition according to claim 1, wherein fusion bonding between each hydroxyapatite nanocrystal particles is prevented.

8. A method of producing a medical composition, which does not contain gelatin, the method comprising mixing a carrier in particle form and a sufficient number of cells in such a manner that the number, per carrier, of said cells to be mixed is less than or equal to $1 \times 10^{10}$, the carrier having (i) a support made from a bioabsorbable polymer particle and (ii) a surface layer made from hydroxyapatite nanocrystal particles, which have diameters of 25 nm to 500 nm, and provided on the support; wherein the particle diameter of the carrier is not less than 10 μm and not greater than 200 μm, and wherein the ratio by weight of said carrier to said cells is from 1/10 to 10/1 and said cells are myelomonocytic cells; such that said sufficient number of cells, which are effective to generate new blood vessels in a living subject, are caused to adhere directly onto the surface layer of said carrier by adhesive ability of the cells.

* * * * *